(12) United States Patent
Bigelow

(10) Patent No.: US 6,221,314 B1
(45) Date of Patent: Apr. 24, 2001

(54) AIR ACTINISM CHAMBER APPARATUS AND METHOD

(76) Inventor: Wil Bigelow, 400 Twelfth St., Suite 23, Modesto, CA (US) 95354

( * ) Notice: Subject to any disclaimer, the term of this patent is extended or adjusted under 35 U.S.C. 154(b) by 0 days.

(21) Appl. No.: 08/963,802

(22) Filed: Nov. 4, 1997

(51) Int. Cl.$^7$ .................................. A61L 2/00; A62B 7/08
(52) U.S. Cl. .................................. 422/24; 96/224; 55/487; 55/286; 250/432 R; 422/121; 422/186; 422/186.3
(58) Field of Search .................................. 422/24, 120, 121, 422/186, 186.3; 96/224, 16; 55/487, 286; 250/432 R, 436, 435, 492.1, 504 R

(56) References Cited

U.S. PATENT DOCUMENTS

| | | | | |
|---|---|---|---|---|
| 1,674,764 | * | 6/1928 | Dauphinee | 55/487 |
| 2,279,810 | | 4/1942 | Arnott | 422/24 |
| 2,495,034 | | 1/1950 | Sullivan | 422/24 |
| 2,732,501 | | 1/1956 | Blaeker | 422/24 |
| 3,094,400 | | 6/1963 | Blanton | 55/102 |
| 3,576,593 | | 4/1971 | Cicirello | 422/24 |
| 3,674,421 | | 7/1972 | Decupper | 422/24 |
| 3,744,216 | | 7/1973 | Halloran | 55/102 |
| 3,745,750 | | 7/1973 | Arff | 55/102 |
| 3,750,370 | | 8/1973 | Brauss et al. | 55/279 |
| 3,757,495 | | 9/1973 | Sievers | 55/279 |
| 3,768,970 | * | 10/1973 | Malmin | 422/121 |
| 3,798,879 | | 3/1974 | Schmidt-Burbach et al. | 55/102 |
| 3,844,741 | | 10/1974 | Dimitrik | 55/102 |
| 4,102,654 | | 7/1978 | Pellin | 55/102 |
| 4,210,429 | | 7/1980 | Golstein | 55/279 |

(List continued on next page.)

FOREIGN PATENT DOCUMENTS

| | | |
|---|---|---|
| 2461290 | 7/1976 | (DE) . |
| 2618127 | 11/1977 | (DE) . |
| 2732859 | 2/1979 | (DE) . |
| 2817772 | 10/1979 | (DE) . |
| 3637702 | 5/1988 | (DE) . |

OTHER PUBLICATIONS

Nagy, et al., "Disinfecting Air with Sterilizing Lamps", Heating, Piping & Air Conditioning, vol. 26., Nos. 1–12, Apr. 1954, pp. 82–87.
Steril–Air, Inc., "Steril–Air UVC Emitters Product Brochure", date unknown, entire brochure.
Sterile–Air, Inc., "Guide to UVC Emitters", date unknown, entire brochure.
Philips Lighting, "Disinfection by UV–radiation", Aug., 1992, entire paper.
Westinghouse, "Sterileamp® Germicidal Ultraviolet Tubes Product Brochure", Mar., 1982, entire brochure.
Vig, U/V Ozone Cleaning of Surfaces, *Treatise on Clean Surface Technology*, vol. 1, 1987, pp. 1–26.
Jensen, "HVAC Technology is Weapon in Fight Against Tuberculosis", *ASHRAE Journal*, Aug., 1997, p. 12.
Georgia Tech Research Corporation, "Emmisions from Mold and Fungus May Cause Indoor Air Problems", 1996, entire article.
Ward, "Is Your Child Allergic to School—Literally?", www.townonline.com, Jan., 1997, entire article.
Layton, "Allergy & Attention Deficit Hyperactivity Disorder (ADHD)", www.allergyconnection.com, 1996, entire article.

(List continued on next page.)

*Primary Examiner*—Krisanne Thornton
(74) *Attorney, Agent, or Firm*—Bernhard Kreten

(57) ABSTRACT

An apparatus and method for ultraviolet irradiation of air for the purpose of removing contaminants from that air is disclosed. A U-shaped ultraviolet bulb enshrouded within a quartz tube provides enhanced contaminant destruction characteristics. By combining a plurality of those bulbs in a chamber that is of polished aluminum, and further combining aluminum filters therewith, added irradiation enhancement is achieved.

44 Claims, 4 Drawing Sheets

U.S. PATENT DOCUMENTS

| | | | | |
|---|---|---|---|---|
| 4255,663 | * | 3/1981 | Lewis | 250/436 |
| 4,750,917 | | 6/1988 | Fujii | 55/6 |
| 4,788,007 | * | 11/1988 | Baron | 252/589 |
| 4,931,654 | | 6/1990 | Horng | 250/436 |
| 4,981,651 | * | 1/1991 | Horng | 422/24 |
| 5,185,015 | * | 2/1993 | Searle | 96/16 |
| 5,200,156 | | 4/1993 | Wedekamp | 422/186.3 |
| 5,225,167 | | 7/1993 | Wetzel | 422/121 |
| 5,288,461 | * | 2/1994 | Gray | 422/24 |
| 5,334,347 | | 8/1994 | Hollander | 422/24 |
| 5,382,805 | * | 1/1995 | Fannon et al. | 250/504 R |
| 5,439,642 | * | 8/1995 | Hagmann et al. | 422/22 |
| 5,466,425 | * | 11/1995 | Adams | 422/24 |
| 5,492,557 | | 2/1996 | Vanella | 96/16 |
| 5,523,057 | | 6/1996 | Mazzilli | 422/121 |
| 5,558,158 | | 9/1996 | Elmore | 165/122 |
| 5,656,242 | | 8/1997 | Morrow et al. | 422/121 |
| 5,730,770 | * | 3/1998 | Greisz | 55/487 |
| 5,853,676 | * | 12/1998 | Morgan | 422/186.3 |

OTHER PUBLICATIONS

Krajick, "The Floating Zoo", *Discover*, Feb., 1997, pp. 66–73.

Sacramento Municipal Utililty District, "Water Water Everywhere, But . . . ", *On Center*, Second Quarter, 1997, p. 1.

Bayer, et al., "Study Suggests Some VOCs Caused by Molds and Fungi", *ASHRAE Journal*, Oct., 1996, p. 12.

* cited by examiner

AIR ACTINISM CHAMBER APPARATUS AND METHOD

FIELD OF THE INVENTION

This invention relates generally to air cleansing devices. More particularly, this invention relates to ultraviolet irradiation and filtration devices.

BACKGROUND OF THE INVENTION

Ultraviolet (UV) light in the form of germicidal lamps has been used since the early 1900's to kill the same types of microorganisms that typically cause the same types of problems today. Since then, UV radiation in the short wave or C band range (UVC) has been used in a wide range of germicidal applications to destroy bacteria, mold, yeast and viruses. After World War II, the use of UVC rapidly increased. UVC is generally understood to exist in the 180 nm to 280 nm wave length area. Typical examples included hospitals, beverage production, meat storage and processing plants, bakeries, breweries, pharmaceutical production and animal laboratories; virtually anywhere microbial contamination was of concern. Early UVC strategies primarily consisted of an upper air approach. This method directed a beam across the ceiling of a room.

During the 1950's when tuberculoses infections were on the rise, the use of UVC became a major component in the control and irradiation of TB. It was discovered that by placing UVC lamps in the air handling equipment, they could initially be more effective.

However, certain conditions found within the air handling systems drastically reduced UVC performance. Moving air, especially below 77° F., over the tubes decreased the output and service life of conventional UVC products and thus their ability to destroy viable organisms. The use of UVC and HVAC systems virtually disappeared over the next decade due to the introduction of new drugs, sterilizing cleaners and control procedures combined with the performance problems of UVC lamps and air handling systems (reduced output, short tube life, and high maintenance). In order for UVC to be effective in the "hostile" environment of indoor central air circulating systems (or HVAC systems), a new method of producing effective UV had to be developed.

The ability of ultraviolet light to decompose organic molecules has been known for a long time, but it is only recently that UV cleaning of surfaces has been explored. In 1972, it was discovered that ultraviolet light could clean contaminated surfaces. Plus, it was learned that there exists a predictable nanometer location of absorption of ozone and organic molecules. It was then learned that the combination of ozone and UV could clean surfaces up to two thousand times quicker than one or the other alone. However, from testing it can be seen that the destructive potential of a combination of UVC and ozone for system components is detrimental. The negative side effects of ozone are now known.

In 1972, tests were conducted using a quartz tube filled with oxygen. A medium pressure mercury (Hg) UV source which generated ozone was placed within centimeters of the tube. A several thousand angstrom thick polymer was exposed to this and was depolymerized in less than one hour. The major products of this reaction were water ($H_2O$) and carbon dioxide ($CO_2$). It was discovered that UV (300 nm and below) and oxygen played a major role in depolymerization. In 1974, research concluded that during such cleaning, the partial pressure of $O_2$ decreased and that of $CO_2$ and $H_2O$ increased, suggesting breakdown.

It was also discovered that the absorption coefficient of $O_2$ increases rapidly below 200 nm with decreasing wave lengths. A 184.9 nm wave length (optimal spectral line for ozone generation) is readily absorbed by oxygen, thus leading to the generation of ozone ($O_3$). Ozone may be generated at undetectable levels at other wave lengths below 200 nm. Therefore, radiation emission below 200 nm was found undesirable.

Similarly, most organic molecules have a strong absorption band between 200 nm and 300 nm. A wave length of 253.7 nm is useful for exciting and disassociating contaminant molecules. 265 nm was thought to be the optimal spectral line for germicidal effectiveness. The 253.7 nm wave length is not absorbed by $O_2$, therefore, it does not contribute to ozone generation, but it is absorbed by most organic molecules and by ozone ($O_3$). Thus, when both wave lengths are present, ozone is continually being formed and destroyed. Unfortunately, previously existing lamps operated between 250 nm and 258 nm, peaking at 254 nm, missing out on the optimal 265 nm goal.

With regard to HVAC systems, biological contaminants are difficult to control because they grow in our moist, indoor environment. The most common strategy is to try to use an effective air system filter to rid indoor air of biological contaminants. While this is an important element of cleaning air, this has its problems. Most filters are inadequate because of the many organisms that pass right on through the filter. Also, any organisms that collect on the filter can form germ colonies that may soon contaminate passing air. Further, if the filter should be too efficient, it blocks the passage of air and creates back pressure, causing the blower to struggle to move air through the system. Furthermore, when the system is turned off, natural temperature differences between the system and indoor air spaces cause convection or back draft flow into the supply ducts (bypassing the filter). This causes contaminants to be pulled back into the duct work, implanting microbes in the air flow duct cavity. These new cultures become added sources of contaminant.

In the past, to try to eliminate the biological contaminants in ducts, a common strategy was to clean the ducts followed by a biocide treatment. But this has its draw backs also. Most biological contaminants return and are active in the treated area within three months. Further, if the system is being treated for severe contamination such as legionela, an acid wash of the coil is common. This is not only expensive, but can shorten the life of the equipment. Furthermore, all biocide used in the ducts are chemical based, leaving potential toxic vapors and chemical pollutants circulating in the system as well. For obvious health reasons, the preferred way to control biological contaminants is through natural, non-polluting strategies.

As indicated above, the effective killing power of UV seemed to be greatest at 265 nm. However, conventional UV has its maximum intensity at 254 nm. Furthermore, the intensity degrades as a function of temperature and distance. This was due to the conventional tubes being designed as long, straight lamps.

The following prior art reflects the state of the art of which applicant is aware and is included herewith to discharge applicant's acknowledged duty to disclose relevant prior art. It is stipulated, however, that none of these references teach singly nor render obvious when considered in any conceivable combination the nexus of the instant invention as disclosed in greater detail hereinafter and as particularly claimed.

SUMMARY OF THE INVENTION

An air cleaning apparatus is disclosed including UV lamps, aluminum filters, and a polished aluminum housing. The UV lamps include a U-bend crystal of quartz, ruby, or sapphire contained within a quartz sleeve. Useful substances for containment within the U-bend bulb are mercury, argon, gallium, iron, xenon or krypton. Between the sleeve and lamp, certain gases (nitrogen or atmospheric gases) are contained therein or the area is possibly evacuated. There are advantages and disadvantages to each. By using a mixture of above gases and/or by varying the electrical charge, one can increase the bandwidth to about 240 nm to about 280 nm, including the 265 nm optimum wave length. Further, increased electrical charge can increase bandwidth and spectral line output from 240 nm to 360 nm for more germicidal effect (UVC/UVB).

Polished aluminum filters and chamber walls are also included in this invention. The treated, polished aluminum alloy provides enhanced reflectivity for the UV rays to enhance the irradiation of particulate flowing through the filters and by the lamps. The aluminum filters have an additional special feature in that one side of the filter is of a coarse mesh whereas the other side of the filter is of a fine mesh. Air flow is from the coarse side to the fine side of one filter, past the UV bulbs, through the fine side, and out the coarse side of another aluminum filter and then back into the duct work of an HVAC system. By providing treated, polished aluminum surfaces surrounding the UV lamps, irradiation is enhanced significantly.

An alternate embodiment in the form of a portable air cleaning device is also described herein. The purpose of the portable device is to clean a single room with a similar system as described hereinabove, but also including a fan built into the portable unit to move through the system.

Another embodiment is described wherein a UV lamp array is mounted exterior to a compressor coil of an HVAC system thereby allowing for cleansing of contaminants contained on the coil and fin structure of the compressor. It has been known that this is a breeding ground for microorganisms and cleansing of this breeding ground will enhance cleansing of the entire HVAC system.

OBJECTS OF THE INVENTION

Accordingly, it is a primary object of the present invention to provide an ultraviolet ray actinism chamber for destroying contaminants thereby.

Another object of the present invention is to avoid the production of ozone in such a system.

Another object of the present invention is to provide increased UV bandwidth to so increase the "killing" power of the UV system.

Another object of the present invention is to maintain a substantially constant temperature around the UV bulb.

Another object of the present invention is to increase UV reflectivity in and around the UV bulbs to enhance the UV irradiation.

Another object of the present invention is to provide self cleaning filters for a UV system.

Another object of the present invention is to provide better, yet shorter lamp lengths to fit in conventional HVAC systems.

Yet another object of the present invention is to enhance the bulb life of a UV bulb for such a system.

Viewed from a first vantage point, it is an object of the present invention to provide an apparatus for purging impurities from ambient conditions, comprising, in combination, a source of radiation in operative communication with the ambient conditions, and means for maintaining the source in a preferred temperature range to promulgate radiation emissivity.

Viewed from a second vantage point, it is an object of the present invention to provide a method for sterilizing air, the steps including, passing the air adjacent a source of ultraviolet light, and resisting temperature drop of the ultraviolet light caused by the passage of the air.

Viewed from a third vantage point, it is an object of the present invention to provide a chamber for cleansing ambient air, comprising, in combination, an air inlet, an air outlet, the chamber interposed and communicating between the inlet and outlet, a source of radiation in the chamber, the chamber imperforate to the radiation, and the chamber having an interior surface with means for reflecting substantially all the radiation.

These and other objects will be made manifest when considering the following detailed specification when taken in conjunction with the appended drawing figures.

DESCRIPTION OF PREFERRED EMBODIMENTS

Figure 1:
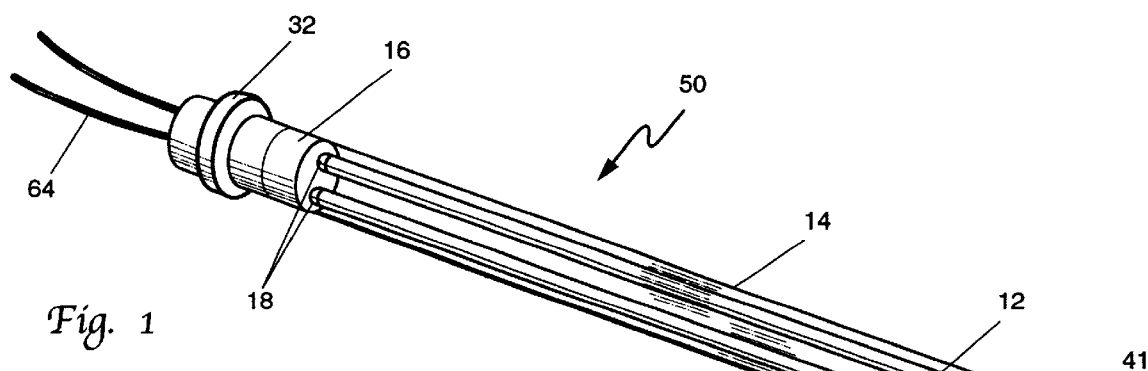
FIG. 1 is a perspective view of the UV lamp of the present invention.
Figure 2:
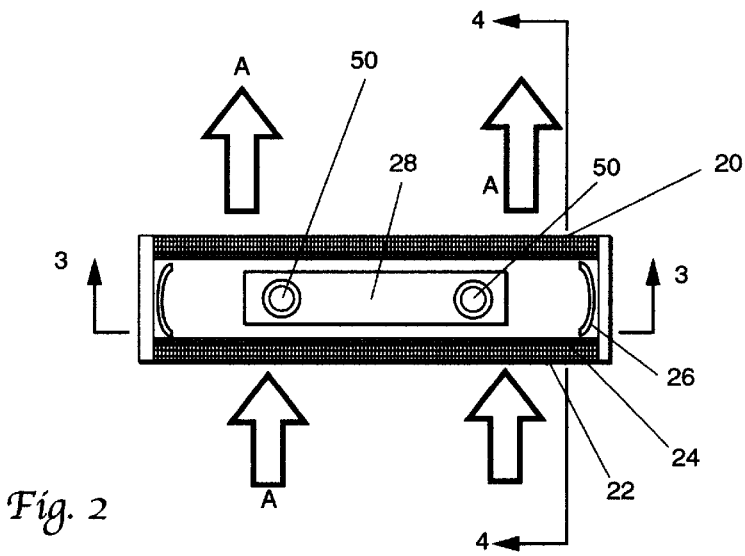
FIG. 2 is a top view of the invention.
Figure 3:
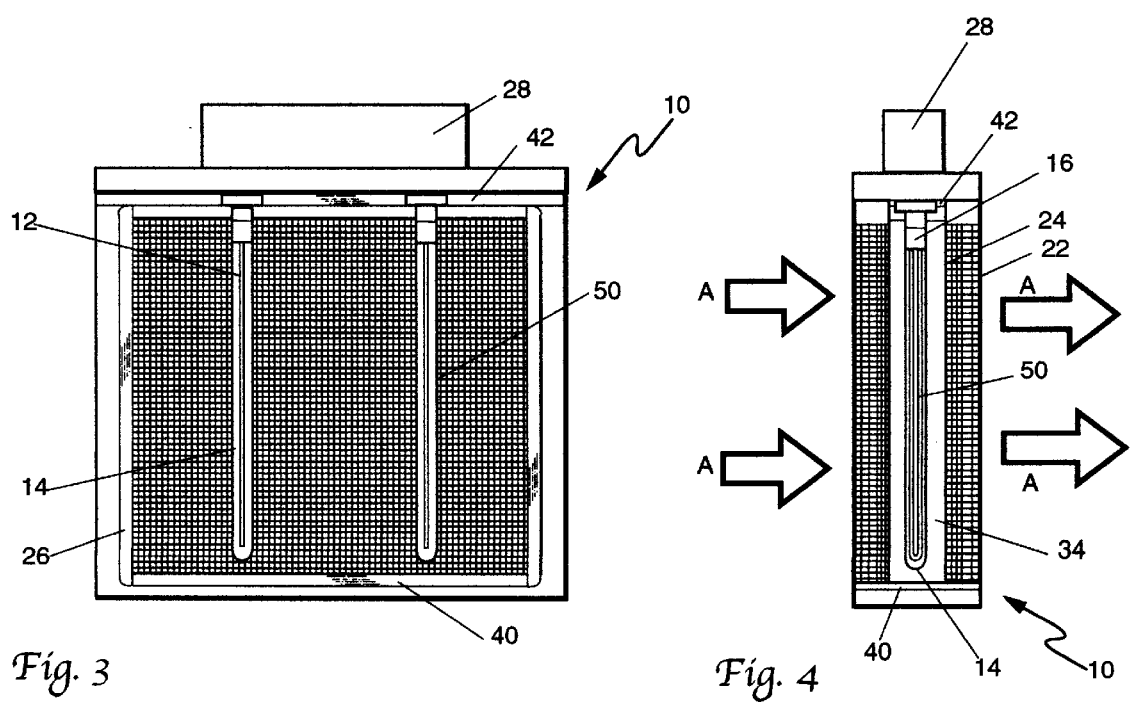
FIG. 3 is a cross-sectional front view taken along lines 3—3 of FIG. 2.
Figure 4:
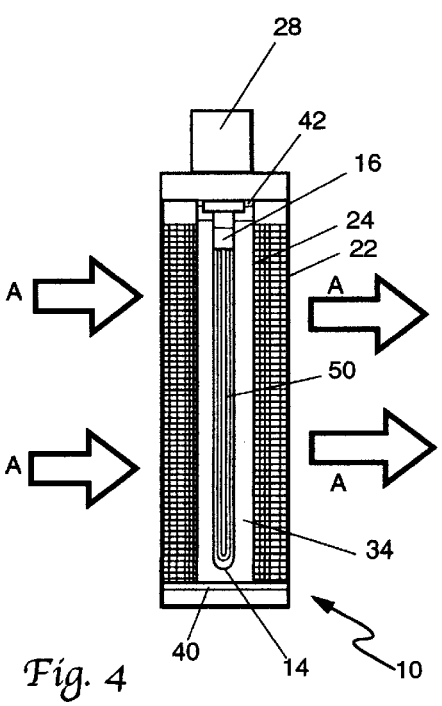
FIG. 4 is a cross-sectional side view taken along lines 4—4 of FIG. 2.

Considering the drawings, wherein like reference numerals denote like parts throughout the various drawing figures, reference numeral 10 is directed to the air actinism chamber according to the present invention.

The invention consists of three main components: UV lamp 50, photon chamber 34 and filters 20. Each component will be described more particularly below.

Figure 8:
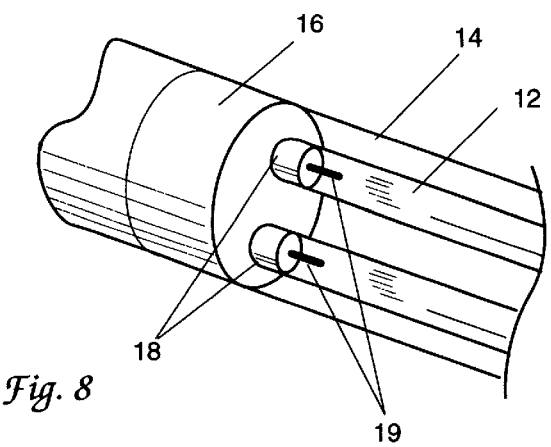
FIG. 8 is a perspective view of the electrode connection of the invention.

As seen in FIGS. 1 and 8, UV lamp 50 consists of a U-shaped UV quartz, ruby, or sapphire crystal 12 (with quartz being preferred), a quartz sheath 14, lamp coupling overlay 16, lamp base 32, U-shaped bulb gases 41, and lamp gas 44. U-shaped bulb 12 is preferably a quartz glass tube up to fifty inches long that is bent at the center to form a U-shaped bulb filled with one or more of the following: mercury, argon, iron, gallium, xenon or krypton. Aluminum metal or ceramic material is machined for the base 32 of the lamp for holding both the lamp tube 12 and electrode igniters 18. That, preferably aluminum coupling 16 allows for good heat transference resulting from the heating of electrodes 18 inside the aluminum coupling 16. That convection heat will be used to maintain its own stabilizing environment around the U-shaped bulb 12 and within the quartz sleeve 14 regardless of ambient temperatures.

Once the U-shaped bulb 12 is mounted onto the aluminum coupling 16 at the point where electrodes 18 extend from within the coupling 16, a gas or gas mixture is sealed within quartz safety shield sleeve 14. That gas or gas mixture is preferably comprised of nitrogen, ordinary air, or evacuated space. By using just air, an approximately 3% loss of intensity of UV is suffered, but certain other costs are lessened. The 3% loss could be eliminated by evacuating the space, however, heat convection does not work as well without gases. Nitrogen gas hermetically sealed under the shell 14 seems to be best, but manufacturing is more complicated.

Figure 5:
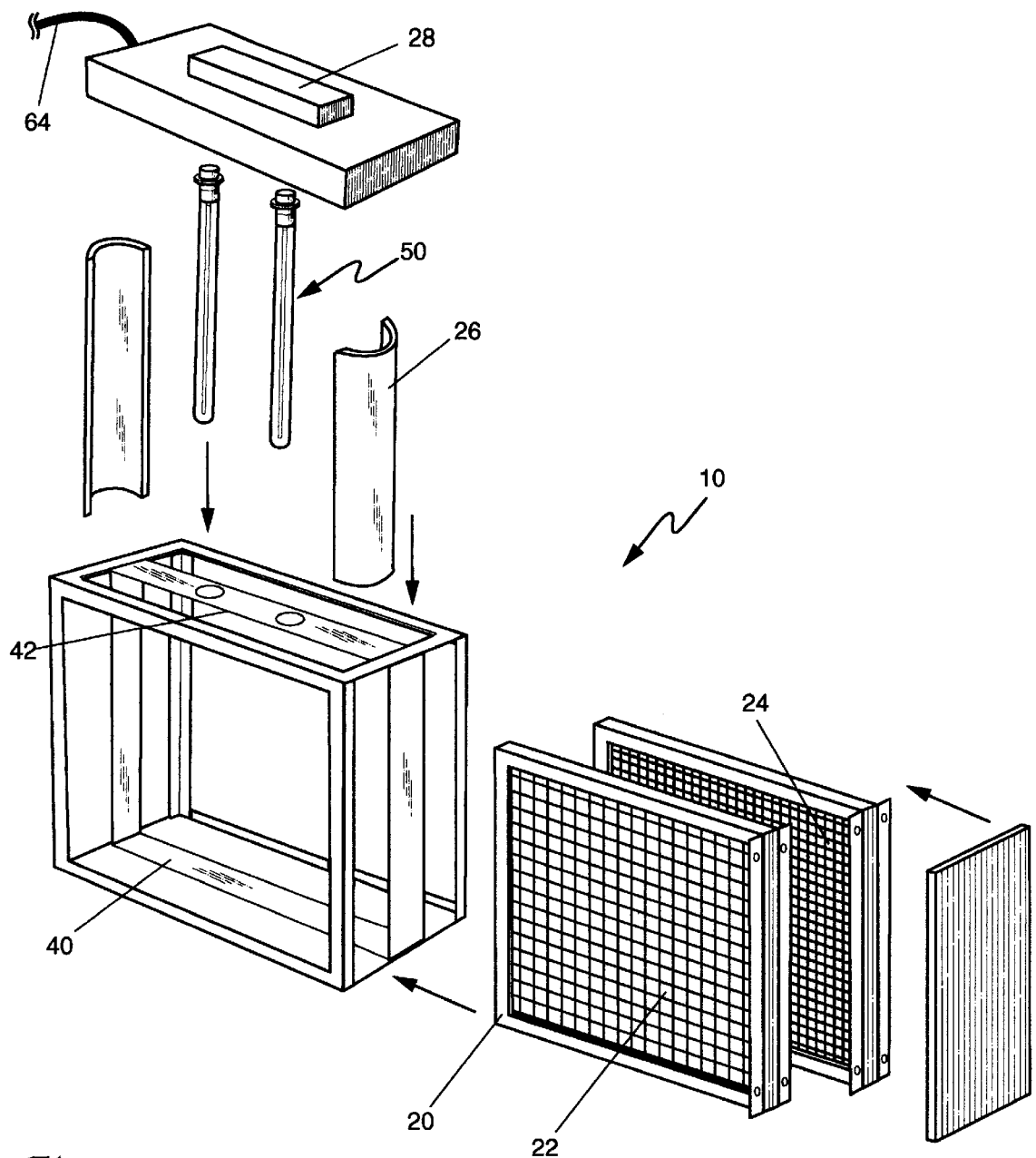
FIG. 5 is an exploded parts perspective view of the invention.

By sealing the U-shaped quartz bulb 12 within shield 14 a constant temperature around bulb 12 is maintained at approximately 80° F. to 90° F. This has been found to be the case even when ambient air temperatures are as low as 45° F. The entire lamp 50 coupled to a proper power supply, as seen in FIGS. 1 and 5, then, for all normal intents and purposes, has the ability to maintain the highest level of intensity regardless of surrounding air temperature or air speed.

UV lamp 50 provides a broader bandwidth compared to conventional UV lamps. As described above, conventional UV lamps emit a bandwidth of about 250 nm to 258 nm. UV lamp 50 provides a bandwidth of about 240 nm to 280 nm, including the optimal 265 nm wavelength and provides approximately six times the UV intensity of conventional lamps at colder temperatures. Furthermore, this is achieved while ambient air temperature around UV lamp 50 is 45° F. to 90° F. Although more power may be required, it has also been discovered that operation at "medium-pressure" will achieve a bandwidth of 230 nm to 380 nm, with an excellent spike at 264 nm. Another optimum point has also been discovered between 310 nm and 340 nm. So, although greater power, and therefore cost, may be required, greater particulate destruction is possible.

The chamber is shown in FIGS. 2 through 5. Lamps 50 are then mounted into housing 28 that includes the electronics and power supply to drive the lamps 50. The power supply is preferably either a matched 110 or 220 volt AC input power supply having a power cord 64. To start the lamp, the power supply sparks the UV gas core 44 and ignites it from a cold start with a temporary voltage spike of about 3,000 volts passing through electrodes 18 and wires 19 to the substances contained within bulb 12. Once the substances are ignited by this starting voltage, the power supply output voltage adjusts down to an operating voltage of about 200 volts to 240 volts AC. By inserting lamps 50 into a chamber of an HVAC unit, UV irradiation of air flowing over and by the lamps 50 is achieved. However, the actinism in the chamber can be enhanced by using special aluminum filters 20 and reflective surfaces within chamber 34.

UV ray reflection can be accomplished by several surface types. Magnesium Oxide, for instance, has been found to achieve the greatest reflectivity (75% to 90%), but is not suited for normal use due to its negative properties. Polished aluminum alloy (treated with Alzak), on the other hand, can achieve up to 95% reflectivity and is well suited to production and manufacture. Typical duct liner reflects 0% to 1% of UV rays which is a draw back of the prior art. Even stainless steel only achieves 25% to 30% reflectivity. Therefore, treated aluminum alloy is preferred.

Figure 10:
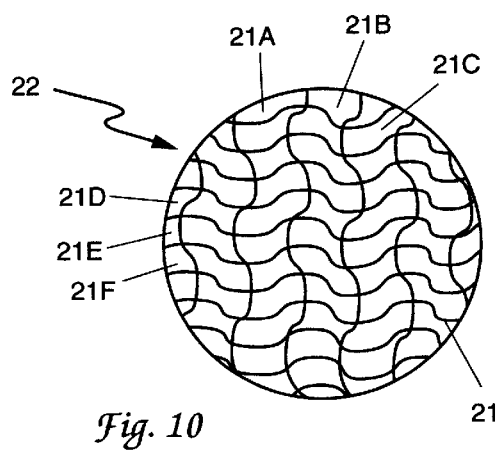
FIG. 10 is a top cutaway view of the coarse filter weave.
Figure 11:
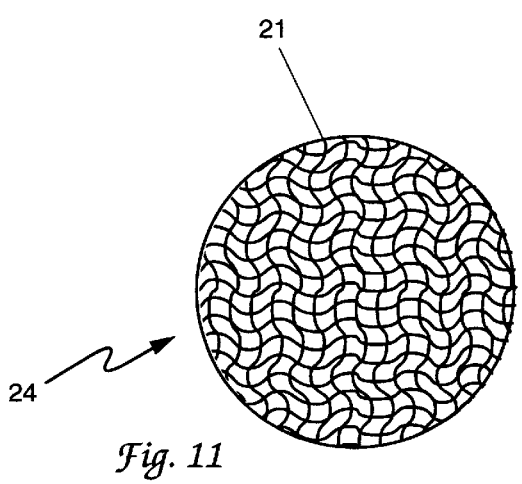
FIG. 11 is a top cutaway view of the fine filter weave.

First, with regard to the filters, a two layered filter constructed of buffed aluminum is preferred. A first coarse layer 22 on an outside of the filter 20 and a second fine mesh layer 24 on the inside of the filter is preferred, wherein the mesh is a wavy aluminum strand weave 21 (FIGS. 10 and 11). That weave may also consist of ribbons of aluminum strands 21A, 21B, 21C interwoven with other such ribbons 21D, 21E, 21F, as shown in FIG. 10. As air flows through the coarse mesh 22 large particulate can be captured and irradiated within the filter before exiting through fine mesh 24. Additionally, because the mesh is polished aluminum and of a reflective nature, reflection of the UV rays is thereby enhanced. Particles trapped within the filter will be bombarded with UV until destroyed, thereby causing the filters to be self-cleaning within the effective irradiation range.

Furthermore, by providing curved side panels 26 running parallel to the lamp that are also made of treated aluminum and polished, reflection is additionally enhanced. The curvature tends to reflect UV rays back toward the central portion of the chamber 34. By also providing wall 42 and bottom wall 40 of a polished aluminum material, maximum reflective irradiation is achieved. The UV rays will either strike particulate directly or be reflected about the chamber enhancing the irradiation bombardment. Certainly, by sizing the chamber 34 appropriately, it could be retrofitted within existing certain HVAC filter housings without modification to the existing housings. However, where an HVAC unit is of an unusual size, minor modifications may be rendered so to fit chamber 34.

Figure 9:
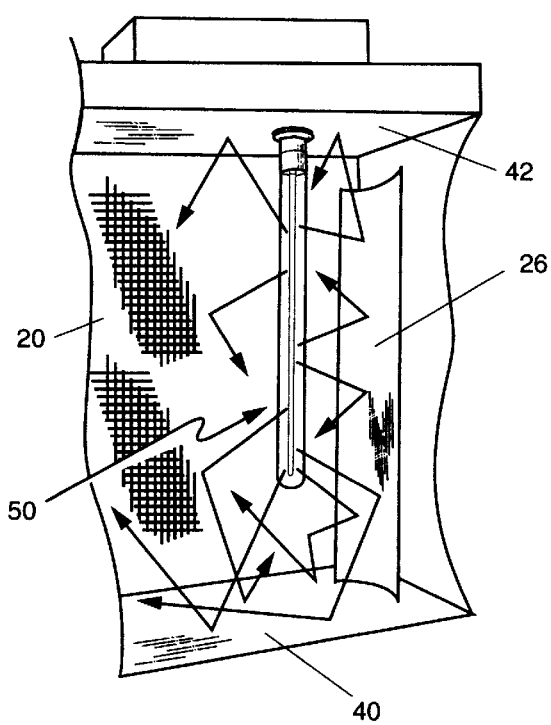
FIG. 9 is a cutaway view of the chamber of the invention showing rays bouncing within the chamber of the invention.

In use and operation, air A traveling through the duct work of a HVAC system will travel through a first aluminum filter 20 by way of its coarse mesh 22 and then its fine mesh 24. Thereafter, the air enters chamber 34 and flows by UV lamps 50, the whole time being irradiated. The air then exits the actinism chamber 34 through the mesh 24 of another aluminum filter 20 and out through coarse mesh 22. Thereafter, having been irradiated and filtered, the air is returned to the HVAC ducts. Any particulate remaining in filter 20 mesh will continue to be irradiated until destroyed by UV lamps 50 as seen in FIG. 9.

Figure 6:
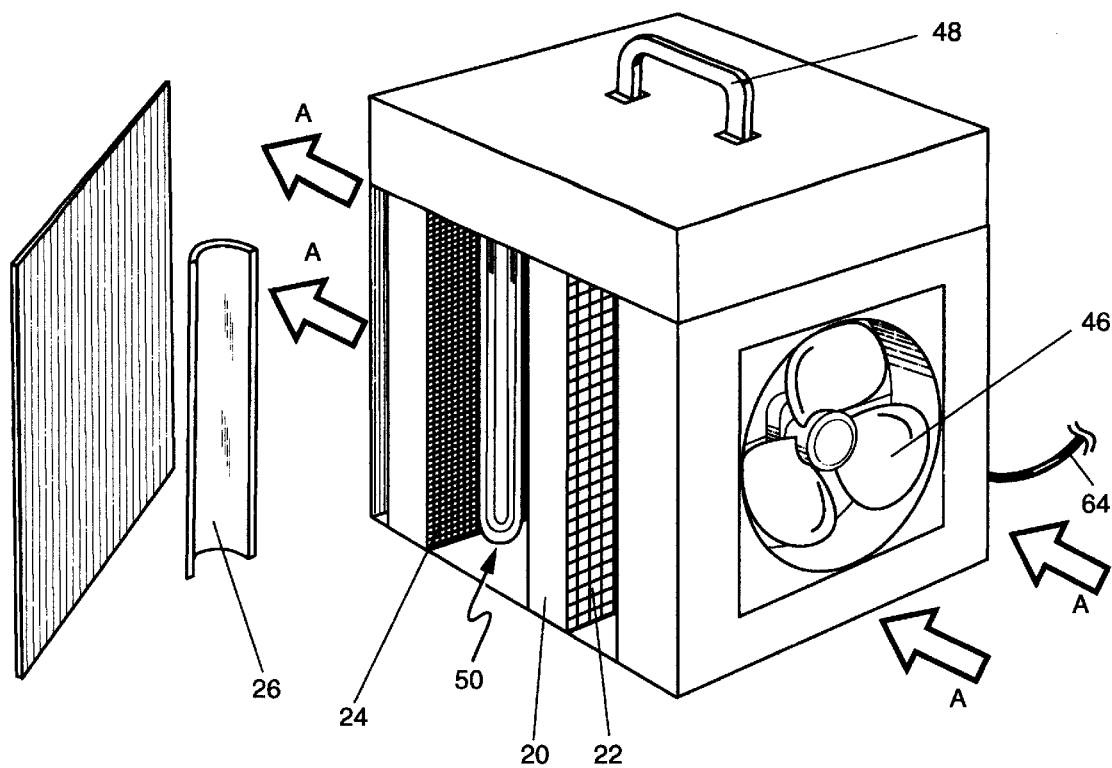
FIG. 6 is a perspective view of a portable alternate embodiment of the invention with a side panel and curved reflective plate projected.

The above-described configuration is ideal for insertion into the return of an HVAC system. FIG. 6 depicts a similar, but alternative embodiment for portable use within a room. Fan 46 provides for the air flow A of this portable device through similar but smaller aluminum filters 20. Between the filters 20, again are maintained one or more UV lamps 50. To transport this item, handle 48 is also provided. Reflective enhancement of the radiation is likewise caused by a plurality of polished aluminum surfaces throughout the inside of the chamber. This is an ideal apparatus for cleaning the air in a single room.

Figure 7:
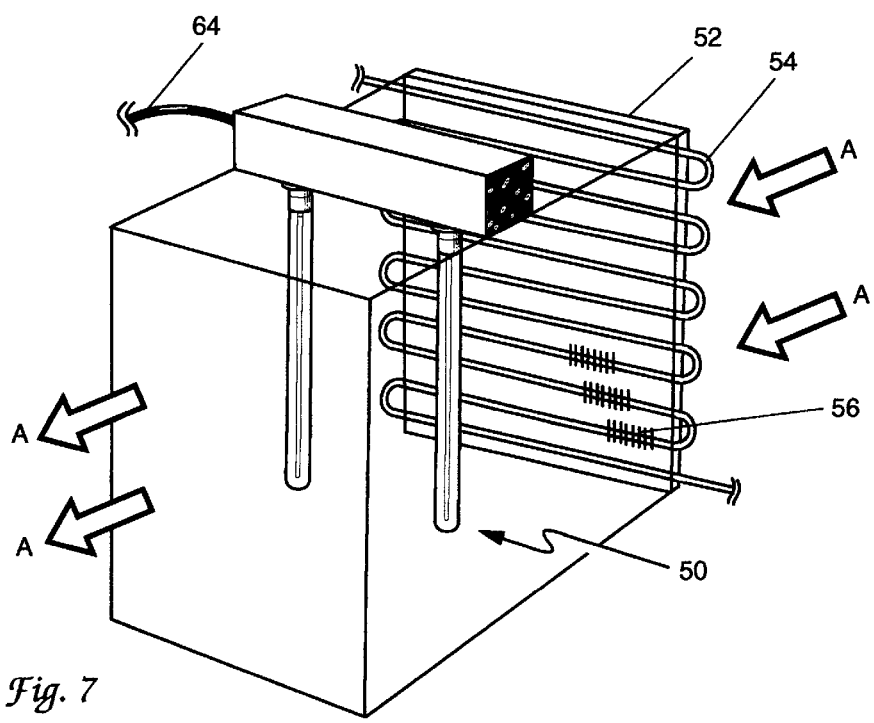
FIG. 7 is a perspective view of an external alternate embodiment of the invention.

FIG. 7 depicts another alternate embodiment for use with an external HVAC device. An evaporative coil 54 coupled to a typical compressor 52 having fins 56 thereby is depicted in FIG. 7. To prevent contamination build-up and to destroy contamination build-up on or about coil 54, UV lamp or lamps 50 are mounted near coil 54. By continuing the lamps 50 in an "on" setting, and additionally using the reflective properties of the aluminum fins, any contamination on or near the coils is eliminated. By maintaining this area in a clean manner, air flow over the area and into the duct work of an HVAC system will be less likely to carry such contamination.

Moreover, having thus described the invention, it should be apparent that numerous structural modifications and adaptations may be resorted to without departing from the scope and fair meaning of the instant invention as set forth hereinabove and as described hereinbelow by the claims.

I claim:

1. An apparatus for purging impurities from ambient conditions, comprising, in combination:
   a source of ultraviolet radiation in operative communication with the ambient conditions; and
   means for maintaining said source in a preferred substantially constant temperature range of between approximately 80° F. to 90° F. to promulgate radiation emissivity for purging substantially all impurities from the ambient conditions.

2. The impurity purging apparatus of claim 1 wherein said temperature maintenance means is an envelope circumscribing said source of radiation to capture and retard thermal migration and promulgate said emissivity.

3. The impurity purging apparatus of claim 2 wherein said source of radiation is an ultraviolet emitter.

4. The impurity purging apparatus of claim 3 wherein said envelope is a sheath for containing heat and allowing the emission of ultraviolet rays.

5. The impurity purging apparatus of claim 4 wherein said sheath is formed from a quartz material.

6. The impurity purging apparatus of claim 5 wherein said ultraviolet emitter includes a quartz tube.

7. The impurity purging apparatus of claim 5 wherein said ultraviolet emitter includes a sapphire tube.

8. The impurity purging apparatus of claim 5 wherein said ultraviolet emitter includes a ruby tube.

9. The impurity purging apparatus of claim 6 wherein said quartz tube contains therewithin one or more substances taken from a family of substances characterized in that electrical excitation of said substances emits ultraviolet radiation.

10. The impurity purging apparatus of claim 9 wherein an interior of said quartz sheath further contains nitrogen, air, or evacuated space.

11. The impurity purging apparatus of claim 10 wherein said quartz tube is U-shaped having electrodes coupled to the termini of said U-shaped tube.

12. The impurity purging apparatus of claim 11 wherein said electrodes are coupled to a heat conductive housing.

13. The impurity purging apparatus of claim 12 wherein said housing is formed from aluminum.

14. The impurity purging apparatus of claim 12 wherein said housing is formed from ceramic.

15. The impurity purging apparatus of claim 13 wherein said ultraviolet emitting substances are taken from the family of substances including mercury, argon, iron, gallium, xenon, or krypton.

16. A method for sterilizing air, the steps including:
    passing the air adjacent a source of ultraviolet light; and
    maintaining the ultraviolet light at an optimal operating temperature between 80° F. to 90° F. by preventing temperature drop of the ultraviolet light's optimal operating temperature caused by the passage of the air over the light.

17. A chamber for cleansing ambient air, comprising, in combination:
    an air inlet;
    an air outlet;
    said chamber interposed and communicating between said inlet and outlet;
    a source of radiation in said chamber, said chamber imperforate to the radiation;
    a temperature maintaining envelope circumscribing said radiation source to maintain the temperature approximately 80° F. to 90° F.;
    said chamber having an interior surface with means for reflecting substantially all the radiation; and
    further comprising a pair of filters, one said filter mounted up stream and one said filter mounted downstream from said radiation source wherein said filters have restrictive means on a surface thereof facing said radiation source.

18. The chamber of claim 17 wherein said reflective means comprises polished aluminum coextensive with said interior surface of said chamber.

19. The chamber of claim 17 wherein said restrictive means is a woven mesh with a less densely woven mesh on a side of said filter facing away from said radiation source.

20. The chamber of claim 19 wherein said filters are made of polished aluminum.

21. The chamber of claim 20 wherein said interior surface is formed from two sidewalls coupled to an upper wall and said filters lie normal to the airpath and perpendicular to said walls.

22. The chamber of claim 21 wherein said sidewalls are arcuate.

23. The chamber of claim 17 further comprising means for altering the air flow in the chamber.

24. The impurity purging apparatus of claim 15 wherein said ultraviolet radiation is emitted at a bandwidth between the range of about 240 nm to 280 nm.

25. The impurity purging apparatus of claim 15 wherein said ultraviolet radiation is emitted at a wavelength of about 265 nm.

26. The impurity purging apparatus of claim 15 wherein said ultraviolet radiation is emitted at a bandwidth of about 230 nm to 380 nm.

27. The impurity purging apparatus of claim 15 wherein said ultraviolet radiation is emitted at a wavelength of about 264 nm.

28. The impurity purging apparatus of claim 15 wherein said ultraviolet radiation is emitted at a bandwidth between about 310 nm and 350 nm.

29. The air sterilization method of claim 16 further including the step of impeding the throughflow of the air past the ultraviolet light.

30. The air sterilization method of claim 29 wherein said impeding step includes providing a plurality of reflective filters normal to the airflow about the source of ultraviolet light.

31. The impurity purging apparatus of claim 15 further comprising:
    a cold start power source operatively coupled to said electrodes whereby said power source is able to provide a 3000 volt voltage spike and thereafter drop to about 200 to 240 volts AC.

32. An air cleansing device, comprising in combination:
    a chamber;
    an air inlet leading into said chamber;
    an air outlet leading out of said chamber;
    said chamber including sidewalls interposed and communicating between said inlet and outlet;
    an ultraviolet radiation source including a UV bulb coupled to said chamber and stationed between said inlet and said outlet;
    means for igniting said bulb;
    means for impeding an air flowpath between said inlet and said outlet to alter flow rate in said chamber;

wherein said flowpath impeding means includes two filters mounted about said UV bulb, one said filter adjacent said inlet and one said filter adjacent said outlet and said filters include a woven mesh with a finer density pore size facing said UV bulb.

33. The device of claim 32 wherein said UV bulb is a U-shaped tube of quartz.

34. The device of claim 32 wherein said ultraviolet radiation is emitted at a bandwidth between the range of about 240 nm to 280 nm.

35. The device of claim 32 wherein said ultraviolet radiation is emitted at a wavelength of about 265 nm.

36. The device of claim 32 wherein said ultraviolet radiation is emitted at a bandwidth of about 230 nm to 380 nm.

37. The device of claim 32 wherein said ultraviolet radiation is emitted at a wavelength of about 264 nm.

38. The device of claim 32 wherein said ultraviolet radiation is emitted at a bandwidth between about 310 nm and 350 nm.

39. The device of claim 33 further comprising electrodes coupled to the termini of said U-shaped tube.

40. The device of claim 39 wherein said electrodes are coupled to a heat conductive housing.

41. The device of claim 32 wherein said chamber includes an interior surface with means for reflecting substantially all radiation.

42. The device of claim 41 wherein said filters include a polished aluminum outer surface.

43. The device of claim 40 further comprising a cold start power source operatively coupled to said electrodes whereby said power source is able to provide a 3000 volt voltage spike and thereafter drop to about 200 to 240 volts AC.

44. The method of claim 16 further including the step of providing a cold powered U-shaped quartz tube sheathed in a quartz shroud for containing heat and allowing emission of ultraviolet rays as the source of ultraviolet light.

* * * * *